US006241788B1

(12) United States Patent
Buentello et al.

(10) Patent No.: US 6,241,788 B1
(45) Date of Patent: Jun. 5, 2001

(54) METHOD OF STABILIZING DYE SOLUTIONS AND STABILIZED DYE COMPOSITIONS

(75) Inventors: Kristin E. Buentello, Newtown; Larry M. Kye, Yardley; Elizabeth Yibin Zhang, North Wales; Victoria Rafalovsky, Yardley; Alan M. Agree, Morrisville, all of PA (US)

(73) Assignee: BetzDearborn Inc., Trevose, PA (US)

(*) Notice: Subject to any disclaimer, the term of this patent is extended or adjusted under 35 U.S.C. 154(b) by 0 days.

(21) Appl. No.: 09/441,662

(22) Filed: Nov. 16, 1999

(51) Int. Cl.$^7$ ..................................... C09B 17/34
(52) U.S. Cl. ................. 8/611; 8/614; 8/617; 8/654; 8/657; 8/607
(58) Field of Search .................. 8/611, 617, 614, 8/607, 602, 654–657; 252/408.1

(56) References Cited

U.S. PATENT DOCUMENTS

| | | |
|---|---|---|
| 3,617,185 | * 11/1971 | Drautz . |
| 4,086,054 | * 4/1978 | Seibert et al. . |
| 4,232,552 | * 11/1980 | Hof et al. . |
| 4,659,481 | 4/1987 | Chen . |
| 4,894,346 | 1/1990 | Myers et al. . |
| 5,032,526 | 7/1991 | Myers et al. . |
| 5,062,962 | 11/1991 | Brown et al. . |
| 5,242,602 | 9/1993 | Richardson et al. . |

FOREIGN PATENT DOCUMENTS

| | | |
|---|---|---|
| 1234038 | 3/1988 | (CA) . |
| 119484 | * 1/1982 | (PL) . |

OTHER PUBLICATIONS

Kugel, Polymeric Material Science and Engineering, Betz Laboratories Inc., Library, vol. 64, pp. 134–135 and abstract, Spring Meeting 1991, Atlanta, Georgia, Proceeding of the American Chemical Society, Division of Polymeric Materials: Science and Engineering, 1991 American Society.
Pal et al., Die Makromoleckulare Chemie, vol. 133, 151–160 (nr. 3263) 1970.
Yamoka et al., Bulletin of Chemical Society of Japan, vol. 51, No. 11, 3182–3192, 1978.
Duxbury, Dyes and Pigments, vol. 25, 131–166, 1994.
Segal et al., Chem. Mater., vol. 9, 2526–2532, 1997.

* cited by examiner

Primary Examiner—Margaret Einsmann
(74) Attorney, Agent, or Firm—Greenblum & Bernstein, P.L.C.

(57) ABSTRACT

Stabilized metachromatic dyes, especially at application concentrations, comprising metachromatic dyes dissolved in one or more non-aqueous solvents, as well as metachromatic dyes dissolved in pH stabilized aqueous solutions. Also, various combinations of treatments are disclosed for stabilizing metachromatic dyes.

49 Claims, 2 Drawing Sheets

METHOD OF STABILIZING DYE SOLUTIONS AND STABILIZED DYE COMPOSITIONS

BACKGROUND OF THE INVENTION

1. Field of the Invention

The present invention relates to the stabilization of metachromatic dyes, and compositions comprising stabilized metachromatic dyes. The present invention is also directed to processes for determining polyionic materials utilizing stabilized metachromatic dye compositions.

2. Discussion of Background Information

Colorimetry is a well-known method of chemical analysis which involves the comparison and matching of a standard color with that of an unknown color to approximate the concentration of a specific component in a sample to be analyzed. When the amount of light absorbed by a given substance in solution is proportional to the concentration of the absorbing species, colorimetry is a simple and accurate method for determining unknown concentrations. For example, if the concentration of a polymer in an aqueous system is to be determined, a sample can be taken, the absorbance of the sample in the presence of a suitable dye can then be measured and compared with a calibration curve to quickly and accurately estimate the concentration of the polymer in the aqueous system. Colorimetry provides advantageous testing since it can easily be performed at the application site. Certain dyes undergo a unique color change upon interaction with polyionic compounds in solution known as metachromasy. Thus, metachromatic dyes are those which undergo a color change upon interaction with polyionic compounds. Any metachromatic dye can be used in a calorimetric test to determine the concentration of a substance, including polycarboxylates, sulfonates, and the like in an aqueous solution. More specifically, when anionic polymers contact a metachromatic dye, the dye molecules align with the anionic charges on the polymers, resulting in a shift in the wavelength of maximum absorbance of the dye molecule. This shift is observable as a color change in the solution containing the dye and the polymer. Thus, since polycarboxylates and sulfonates, which are anionic, induce a metachromatic change in certain dyes, their concentrations in aqueous solutions can be determined calorimetrically by measuring the absorbance, at a specified wavelength, of a solution containing polycarboxylates and/or sulfonates and a metachromatic dye and comparing this absorbance to absorbances of standards having known concentrations of the species being measured.

However, when metachromatic dyes are dissolved in aqueous solutions for use in analytical determinations, fresh samples must be prepared on a daily basis to insure accurate analysis. Aqueous solutions of metachromatic dyes are extremely susceptible to degradation due to a variety of factors, such as light, temperature, dissolved oxygen, pH, etc. For example, when pinacyanol chloride is dissolved in an aqueous solution at a concentration of $9.0 \times 10^{-5}$ molar, the pinacyanol chloride degrades at a rate of approximately 10 to 20% per week. Because of this degradation problem, frequent reagent preparations must be made in the field and this is not practical.

Still further, the instability of known dye solutions leads to disadvantageous results associated with the detection process. These disadvantages result in a lack of reproducibility of results, i.e., consistency of results is difficult to attain on separate days even with the same water sample.

Accordingly, there is a need to provide stable metachromatic dyes that enable simple tests for materials, particularly water treatment polymers, and especially enable simple tests that can be utilized over extended periods of time without the need for formulation in the field.

SUMMARY OF THE INVENTION

The present invention concerns methods for stabilizing metachromatic dyes so that the dyes will not be susceptible to degradation and stabilized compositions comprising the metachromatic dyes. This will ensure that any colorimetry testing using the stabilized dyes can be performed with the added assurance of reproducible results.

The present invention is directed to stabilized metachromatic dye compositions, including aqueous solutions and non-aqueous solutions of metachromatic dye, having a percent change in absorbance of less than about 10% when stored for a period of about one week, more preferably less than about 1% when stored for a period of about one week, even more preferably less than about 3% when stored for a period of about one month, even more preferably less than about 5% when stored for a period of about 3 months, even more preferably less than about 5% when stored for a period of about 6 months, even more preferably less than about 10% when stored for a period of about one year, and even more preferably less than about 5% when stored for a period of about one year.

Further, the present invention is directed to aqueous solutions of metachromatic dye comprising metachromatic dye in an aqueous solvent, the aqueous solvent having a metachromatic dye stabilizing pH.

Still further, the present invention is directed to non-aqueous solutions of metachromatic dye comprising metachromatic dye and non-aqueous solvent, the non-aqueous solution being substantially free of water.

Still further, the present invention is directed to a stabilized metachromatic dye composition for analytical determination of at least one polyionic substance, the metachromatic dye composition including a concentration of metachromatic dye which provides maximum metachromatic absorbance for the at least one polyionic substance when the at least one polyionic substance is present at a concentration of 0.1 to 1.5 ppm, and the metachromatic dye composition has a percent change in absorbance of less than about 10% when stored for a period of about one week.

Still further, the present invention is directed to a stabilized aqueous solution of metachromatic dye comprising metachromatic dye in an aqueous solvent, the aqueous solution having a metachromatic dye stabilizing pH, and a percent change in absorbance of less than about 10% when stored for a period of about one week.

Still further, the present invention is directed to a metachromatic dye solution for analytical determination of at least one polyionic substance comprising metachromatic dye and non-aqueous solvent, the solution being substantially free of water, said metachromatic dye solution including a concentration of said metachromatic dye which provides maximum metachromatic absorbance for the at least one polyionic substance when said at least one polyionic substance is present at a concentration of 0.1 to 1.5 ppm, and said non-aqueous solvent comprises at least one of methanol, ethanol, butanol, isopropanol, propanol, ethylene glycol, methylcellosolve, hexane, pentane, heptane, toluene, xylene, benzene, dichlorobenzene, acetone, ethyl acetate, diethyl ether, acetonitrile and dimethylsulfoxide.

Still further, the present invention is directed to a process for analytical determination of at least one polyionic substance in a sample, comprising forming a mixture by mixing a metachromatic dye solution and the sample, the metachromatic dye solution comprising metachromatic dye and non-aqueous solvent, the solution being substantially free of water, and performing an absorbance measurement on the mixture.

The aqueous solution of metachromatic dye can comprise aqueous solvents having a pH of at least about 8, more preferably a pH of at least about 10, and even more preferably a pH of at least about 11. Preferred pH ranges of the aqueous solvents include a pH range of about 8 to 14, even more preferably a pH range of about 11 to 12, and even more preferably a pH range of about 11 to 11.5. The aqueous solution of metachromatic dye can include at least one basic material, such as a buffer, or a material such as at least one of sodium hydroxide, potassium hydroxide and lithium hydroxide, preferably sodium hydroxide. Moreover, the aqueous solution of metachromatic dye can include at least one non-aqueous solvent.

The metachromatic dye can comprise at least one of pinacyanol chloride, crystal violet, methyl green, malachite green, acridin orange, paraosaniline, nile blue A, neutral red, safrin O, methylene blue, methyl red, brilliant green, toluidine blue, new methylene blue, quinalizarin, tetrachrome, brilliant blue G, and mordant black II, and is preferably pinacyanol chloride.

The non-aqueous solvent can comprise at least one of alcohols, methylcellosolve, hexane, pentane, heptane, toluene, xylene, benzene, dichlorobenzene, acetone, ethyl acetate, diethyl ether, acetonitrile, dimethylsulfoxide, preferably at least one of methanol, ethanol, butanol, isopropanol, propanol and ethylene glycol.

The non-aqueous solution of metachromatic dye can include one or more non-aqueous solvents, preferably a mixture of methanol and ethylene glycol having a preferred 25 vol % of methanol to 75 vol % of ethylene glycol, with the non-aqueous solution preferably having a density at 25° C. of about 0.95 to 1.2 $g/cm^3$, more preferably about 1 to 1.1 $g/cm^3$, and even more preferably about 1 to 1.05 $g/cm^3$.

The non-aqueous solution of metachromatic dye is preferably free of water.

The non-aqueous solvent preferably comprises high purity solvent.

The solutions of metachromatic dye preferably include at least one oxygen scavenger.

The solutions of metachromatic dye preferably are in the substantial absence of oxygen.

The solutions of metachromatic dye preferably are purged with an inert gas.

The present invention is also directed to containers including therein the solutions of metachromatic dye according to the present invention. The container at least reduces the transmission of light, and preferably prevents the transmission of light.

The present invention is also directed to methods of determining materials, such as polyionic materials, preferably polyionic polymers utilizing the metachromatic dye solutions according to the present invention.

DESCRIPTION OF THE DRAWINGS

The above and other features and advantages of the present invention will be made apparent from the following description of the preferred embodiments, given as non-limiting examples, with reference to the accompanying drawings, in which.

DETAILED DESCRIPTION OF THE PRESENT INVENTION

The particulars shown herein are by way of example and for purposes of illustrative discussion of embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how varying forms of the present invention may be embodied in practice.

Unless otherwise stated, all percentages, parts, ratios, etc., are by weight.

Unless otherwise stated, a reference to a compound or component includes the compound or component by itself, as well as in combination with other compounds or components, such as mixtures of compounds.

Further, when an amount, concentration, or other value or parameter, is given as a list of upper preferable values and lower preferable values, this is to be understood as specifically disclosing all ranges formed from any pair of an upper preferred value and a lower preferred value, regardless whether ranges are separately disclosed.

The present invention is directed to stable compositions of metachromatic dyes. According to the present invention, the metachromatic dye composition is stable if the absorbance of metachromatic dye composition changes by less than about 10%, more preferably less than about 5%, even more preferably less than about 3%, and most preferably less than about 1%, when stored for a period of about 1 week, more preferably about 1 month, even more preferably about 3 months, even more preferably about 6 months, even more preferably about 7.5 months, even more preferably about 10 months, and even more preferably about 1 year or more.

In order to determine the change in absorbance of the metachromatic dye composition, an initial absorbance of the metachromatic dye composition is determined 3 minutes after mixing of the metachromatic dye and the solvent at any wavelength in the visible spectrum of 300 to 700 nm to obtain the absorbance data for the initially prepared metachromatic dye composition. While one or more wavelengths can be utilized and/or measurements can be made over the whole spectrum, preferably the wavelength of light is preferably at or about the wavelength that provides maximum absorbance. The metachromatic dye composition, i.e., either the same dye composition that was tested to provide the initial absorbance, another portion of the same metachromatic dye composition, or a metachromatic dye composition that has been formulated to be identical to the metachromatic dye composition tested for absorbance is then stored at ambient temperature, i.e., at 25° C., for the period of time under dark conditions, such as by being stored in an amber container, for which the stability test is to be performed. Absorbance of the metachromatic dye composition is determined at the same wavelength or wavelengths of light as for the initially prepared metachromatic composition. Calculations are then performed to determine the percent change in absorbance.

Still further, the stabilized metachromatic dye compositions according to the present invention are capable of use as metachromatic dyes in analytic determination of polyionic compounds, particularly polyionic compounds including polycarboxylate and/or sulfonate concentrations in aqueous systems.

The present invention is directed to any technique for maintaining the stability of the metachromatic dye composition, and a variety of techniques for providing stability to metachromatic dye compositions are disclosed herein. Furthermore, it is noted that stability techniques disclosed herewith can be utilized individually and in combination with each other.

The present invention is directed to any metachromatic dye that can be stabilized according to the present invention. In particular, metachromatic dyes that are most preferred for the present invention include metachromatic dyes that are suitable for use in colorimetric tests for determining polyionic compounds in aqueous systems, preferably for determining polycarboxylate and/or sulfonate concentrations in aqueous systems. Examples of metachromatic dyes include, but are not limited to, pinacyanol chloride, crystal violet, methyl green, malachite green, acridin orange, paraosaniline, nile blue A, neutral red, safrin O, methylene blue, methyl red, brilliant green, toluidine blue, new methylene blue, quinalizarin, tetrachrome, brilliant blue G, and mordant black II, preferably nile blue A and/or pinacyanol chloride.

The stability of the metachromatic dye composition can be enhanced by any technique that provides stability of the metachromatic dye composition. The following embodiments of the present invention are therefore to be considered non-limiting embodiments setting forth preferred manners of stabilizing metachromatic dye composition, and providing guidelines in order that one having ordinary skill in the art can provide, without undue experimentation, techniques for providing stabilized metachromatic dye compositions according to the present invention.

With the above in mind, it is noted that in one aspect the present invention achieves stabilized aqueous metachromatic dye compositions by providing an aqueous composition of the dye having a pH of at least about 8, more preferably at least about 10, and even more preferably at least about 11, with preferred pH ranges being from about 8 to 14, more preferably from about 10 to 13, even more preferably from about 10.5 to 12.5, even more preferably about 11 to 12, and even more preferably about 11 to 11.5, with one preferred pH value being about 11. For ease of reference the pH or pH range at which the metachromatic dye is stabilized will be referred to herein as the metachromatic dye stabilizing pH. Thus, the terminology metachromatic dye stabilizing pH will be utilized herein to denote a metachromatic dye composition having a stabilizing pH in contrast to a non-stabilizing pH, such as an acidic pH.

The pH of the metachromatic dye composition can be adjusted and/or maintained in various manners to provide the metachromatic dye stabilizing pH without effecting or substantially effecting the coloring changing or substantially changing the coloring changing ability of the metachromatic dye and the metachromatic dye composition, and preferably without changing or substantially changing the absorbance of the metachromatic dye and metachromatic dye composition. For example, basic materials including, but not limited to, at least one of sodium hydroxide, lithium hydroxide, potassium hydroxide, rubidium hydroxide, calcium hydroxide, barium hydroxide, magnesium hydroxide and ammonia. Preferably the basic material is at least one of sodium hydroxide, such as a 1N solution of sodium hydroxide, lithium hydroxide and/or potassium hydroxide.

Additionally, the pH of the metachromatic dye composition can be adjusted and/or maintained using buffer systems that provide the metachromatic dye stabilizing pH without affecting or substantially affecting the coloring changing or substantially changing the coloring changing ability of the metachromatic dye and the metachromatic dye composition, and preferably without changing or substantially changing the absorbance of the metachromatic dye and metachromatic dye composition. Preferably, the buffer system maintains a pH of about 9 to 11 in the metachromatic dye composition. For example, buffer systems include, but are not limited to, potassium carbonate/potassium borate/potassium hydroxide (pH=10), boric acid/potassium chloride/sodium hydroxide (pH=9), sodium hydroxide/glycine/sodium chloride (pH=11), sodium tetraborate (pH=9.18), and tris(hydroxymethyl) amino methane (pH=10.4).

The aqueous metachromatic dye compositions of the present invention can include other solvents therein in addition to water, such as non-aqueous solvents. For examples, other solvents in addition to water can be included in the aqueous metachromatic dye compositions, such as, but not limited to, ethanol, methanol, butanol, propanol, ethylene glycol, methyl cellosolve, and glycol. For example, the volume ratio of water to other solvent can range from about 99 vol % to 1 vol %, more preferably from about 80 vol % to 20 vol %, even more preferably about 75 vol % to 25 vol %, even more preferably about 50 vol % to 50 vol %, even more preferably from about 20 vol % to 80 vol %, and even more preferably from about 10 vol % to 90 vol %, and can even be as low as 1 vol % to 99 vol %.

When the aqueous metachromatic dye composition is utilized in a test the pH of aqueous metachromatic dye composition is preferably adjusted to be at a neutral pH of about 6.5 to 7. Adjustment of the pH can be affected in any manner that lowers the pH while not interfering with the metachromatic dye, such as by adding an acid, such as, but not limited to, sulfuric acid, nitric acid, or a buffer, such as, but not limited to, meta buffer, i.e., 10.1 wt % EDTA (ethylendiaminetetraacetic acid) tetrasodium salt, 11 wt % potassium phosphate monobasic, and 78.9 wt % distilled water.

In another aspect, the present invention achieves stabilized metachromatic dye compositions by providing non-aqueous compositions of the dye. In this regard, it has been discovered that the stability of metachromatic dyes is deteriorated by its inclusion in an aqueous environment. In particular, it is noted that when metachromatic dyes are stored in non-aqueous compositions stable metachromatic dye compositions are obtained.

The non-aqueous metachromatic dye compositions according to the present invention can include water therein, such as trace amounts of water that do not affect the stability of the metachromatic dye compositions. For ease of reference, these compositions are referred to herein as non-aqueous metachromatic dye compositions or solutions. In other words, the non-aqueous metachromatic dye compositions of the present invention can include amounts of water therein whereby the compositions are in conformance with the stability requirements of the present invention. Thus, when referring to a non-aqueous composition that is substantially free of water, such composition is intended to include up to an amount of water whereby the composition conforms with the stability requirements of the present invention. Preferably, the non-aqueous metachromatic dye compositions of the present invention contain, at most, trace amounts of water, and preferably do not include water therein.

The non-aqueous metachromatic dye composition can be formulated using a variety of non-aqueous solvents in which the one or more metachromatic dyes intended to be included in the metachromatic dye composition are soluble. Therefore, in order to determine whether a non-aqueous solvent is a non-aqueous solvent or mixture of non-aqueous solvents that is utilizable in the non-aqueous metachromatic dye composition according to the present invention, a non-aqueous solvent or mixture of the non-aqueous solvents should be mixed with the one or more metachromatic dyes that are intended to be utilized in the non-aqueous metachromatic dye composition to determine if the one or more metachromatic dyes are soluble in the non-aqueous solvent or mixture of non-aqueous solvents. If the one or more metachromatic dyes are soluble in the non-aqueous solvent or mixture of non-aqueous solvents, the non-aqueous metachromatic dye composition can be formulated with the non-aqueous solvent or mixture of non-aqueous solvents and subjected to the herein discussed stabilization test to determine whether stabilization is achieved for the non-aqueous solvent or mixture of non-aqueous solvents.

The non-aqueous solvents can include, but are not limited to, alcohols such as methanol, ethanol, butanol, propanol, isopropanol, ethylene glycol, propylene glycol, glycerin (glycerol); and organic solvents such as methylcellosolve, hexane, pentane, heptane, toluene, xylene, benzene, dichlorobenzene, acetone, ethyl acetate, diethyl ether, acetonitrile, dimethylsulfoxide. Preferred solvents include methanol, ethanol, isopropanol, butanol, propanol and ethylene glycol.

Preferably, the non-aqueous solvent has a density at 25° C. of about 0.95 to 1.2 $g/cm^3$, more preferably 1 to 1.1 $g/cm^3$, and even more preferably 1 to 1.05 $g/cm^3$, with a preferred value of density being about 1 $g/cm^3$. To achieve this preferred density, the non-aqueous solvent can be composed of one non-aqueous solvent that has a density within the preferred range, or a mixture of non-aqueous solvents, with one, some or all of the non-aqueous solvents within the mixture comprising a density that is not within the preferred density range; however, the density of the mixture of non-aqueous solvents will preferably be within the preferred range.

Expanding upon the above, it is noted that single non-aqueous solvent or mixtures of non-aqueous solvents can be utilized in the non-aqueous metachromatic dye compositions of the present invention. In this regard, it is noted that the viscosities of non-aqueous solvents can be lower than desired, whereby non-aqueous metachromatic dye compositions incorporating these non-aqueous solvents can be too volatile. Still further, it is noted that the viscosities of other non-aqueous solvents can be higher than desired, whereby non-aqueous metachromatic dye compositions incorporating these non-aqueous solvents can be too viscous. Therefore, it is preferable that the non-aqueous solvent have a density at 25° C. of about 0.95 to 1.2 $g/cm^3$, more preferably 1 to 1.1 $g/cm^3$, and even more preferably 1 to 1.05 $glcm^3$, with a preferred value being about 1 g/cm 3, or comprise mixtures of non-aqueous solvents, which mixture has a density at 25° C. of about 0.95 to 1.2 $g/cm^3$, more preferably 1 to 1.1 $g/cm^3$, and even more preferably 1 to 1.05 $g/cm^3$, with a preferred value being about 1 $g/cm^3$.

The mixture of non-aqueous solvents of differing densities can comprise various mixtures of non-aqueous solvents, with one preferred mixture being composed of methanol (density of 0.8 $g/cm^3$ at 25° C.) and ethylene glycol (density of 1.1 $g/cm^3$ at 25° C.). Preferably, the higher density non-aqueous solvent is present in the mixture in a range of about 50 vol % to 95 vol %, with the lower density non-aqueous solvent being present in the mixture in a range of about 5 vol % to 50 vol %. Particularly preferred values include wherein the higher density non-aqueous solvent is present in the mixture at about 60 vol %, with the lower density non-aqueous solvent being present in the mixture at about 40 vol %; wherein the higher density non-aqueous solvent is present in the mixture at about 70 vol %, with the lower density non-aqueous solvent being present in the mixture at about 30 vol %; and wherein the higher density non-aqueous solvent is present in the mixture at about 75 vol %, with the lower density non-aqueous solvent being present in the mixture at about 25 vol %. In other words, it is preferred that the volume ratio of higher density non-aqueous solvent to lower density non-aqueous solvent is about 19:1 to 1:1, more preferably about 3:1 to 1.5:1, and even more preferably about 3:1 to 2.3:1. A particularly preferred non-aqueous solvent mixture comprises methanol present in an amount of about 25 volume percent and ethylene glycol present in an amount of about 75 volume percent.

Further beneficial improvements to the metachromatic dye compositions according to the present invention can be achieved by utilizing high purity materials, such as distilled water in the case of aqueous metachromatic dye compositions, such as high purity non-aqueous solvents and high purity viscosity increasing agent or diluents in the case of a non-aqueous metachromatic dye composition.

In the case of non-aqueous solvents, high purity is referred to herein as a purity of at least 99 wt %. It is noted that high purity is usually associated with technical grade materials, as compared to reagent grade materials.

The higher purity materials provide metachromatic dye compositions according to the present invention with at least lower concentrations of interfering agents. For example, low purity materials can add interfering agents, such as iron, calcium and/or magnesium to the metachromatic dye composition, which interfering agents can interference with both the metachromatic dye and the analytical test, such as an analytical test for polyionic polymers.

Further beneficial improvements to the metachromatic dye compositions according to the present invention can be achieved by storing the metachromatic dye composition in an oxygen free or substantially oxygen free environment. The oxygen free or substantially oxygen free environment can be obtained in any manner by which oxygen, such as molecular oxygen, or oxidative components in the composition are avoided and/or removed from the metachromatic dye composition. For example, and without limiting the present invention, an oxygen free or substantially oxygen free environment can be achieved by utilizing one or more of a variety of techniques including storing the metachromatic dye composition in a sealed container, purging the metachromatic dye composition with an inert gas, such as argon or nitrogen, utilizing an oxygen scavenger, such as, but not limited to, sodium sulfite, sodium bisulfite, ascorbate, hydrazine, hydroquinone, benzohydroquinone, or sealing the metachromatic dye composition under vacuum or partial vacuum.

With regard to sealing the metachromatic dye composition in a container, it is noted that the metachromatic dye composition can be sealed in any container that limits diffusion of oxygen into the metachromatic dye composition. Accordingly, the metachromatic dye composition can be contained in a container that is sealed, such as by utilizing a closure element that can seal an opening in the container.

For example, and without limiting the invention, the closure element can include a cap, such as a cap that can be screwed over the opening of the container to seal the opening, a cap that can be sealingly pressed against the opening to obtain a seal between the opening and the cap; or a cork type element, such as a rubber cork that can be inserted into the opening. A particularly preferred container is an 8 oz. Amber Boston Round, 24/400 finish (referring to the threads on neck of bottles) including a 24/400 black phenolic polyseal cone liner as a cap, as distributed by PENN Bottle and Supply Co., Philadelphia, Pa., with the amber container being manufactured by Lawson Mardon Wheaton, Millbille, N.J., and the cap being manufactured by Poly/Seal Corp., Baltimore, Md.

Still further, the containers can comprise completely sealed containers, such as ampoules. In such types of containers, it is often necessary that the container be broken to enable release of the composition contained therein.

With respect to the use of oxygen scavengers, the oxygen scavenger can comprise inorganic and/or organic materials, such as, but not limited to, sodium sulfite, sodium bisulfite, ascorbate, hydrazine, hydroquinone, benzohydroquinone. The oxygen scavenger is preferably added to the metachromatic dye composition during its preparation, or as soon as possible after the metachromatic dye composition is prepared. In the instance where the oxygen scavenger is added after preparation of the metachromatic dye composition, it is preferred that the oxygen scavenger be added to the metachromatic dye composition immediately after its production. Most preferably, the oxygen scavenger is added to the solvent prior to the addition of the metachromatic dye.

With respect to purging with an inert gas, any purging technique can be utilized to remove oxygen from the metachromatic dye composition. In this regard, without limiting the invention, the inert gas, such as nitrogen and/or argon, can be caused to bubble through or pass over the metachromatic dye composition, preferably passed over the metachromatic dye composition. Of importance is that the purging technique is sufficient to remove an effective amount of oxygen to enhance stability of the metachromatic dye composition. Moreover, the purging technique is preferably adapted to remove as little of the solvent as possible, particularly in the case where the solvents are highly volatile. In one exemplary purging technique, a piece of flexible tubing, such as Tygon tubing, is connected to an inert gas tank, such as an argon tank, on one end, and a glass or plastic pipette on the other end. The inert gas tank is turned on, and the gas is gently bubbled through the solution in a container, such as a beaker, an Erlenmeyer flask, etc.

Similarly, any technique for sealing a metachromatic dye composition under vacuum or partial vacuum can be utilized. Thus, for example, the metachromatic dye composition can be placed in a container, and a vacuum pulled on the container and its content to achieve a vacuum of less than about 100 mm of mercury (1 ppm $O_2$), more preferably less than least about 50 mm of mercury (0.5 ppm $O_2$), and even more preferably less than about 20 mm of mercury (0.2 ppm $O_2$).

Moreover, further beneficial improvements to the metachromatic dye compositions according to the present invention can be achieved by storing the metachromatic dye composition in a container that protects the metachromatic dye composition from light, especially ultraviolet radiation. Thus, any container that at least partially limits, and preferably completely blocks, the entrance of light into the metachromatic dye composition, can be preferably utilized to store the metachromatic dye composition. For example, the walls of the container can be constructed from an opaque material that will completely block the entrance of light in the container and/or the container can be placed in a dark environment, such as a cardboard carton or a styrene package. Still further, the walls of the container can be constructed from a translucent material that permits light to partially enter the metachromatic dye composition.

As examples of materials of construction for the container, without limiting the invention, the container can be constructed of glass that is treated and/or colored to prevent or limit penetration of light into the container, such as amber colored glass, plastic containing materials to block or limit the entrance of light, such as materials that will at least limit or block the passage of ultraviolet radiation, or a metal. A preferred amber bottle is obtainable from Nalgene International, and is constructed from HDPE. An opaque container that prevents light transmission can be constructed of Teflon fluorinated ethylene propylene (FEP), which is used for extraordinary chemical resistance. Also a black Teflon FEP container containing a carbon black pigment for zero transmission of both visible and ultraviolet light is also available from Nalgene International.

If the container is constructed from materials that may be an interferant to the metachromatic dye or materials to be analyzed, it is preferred to include a liner and/or a coating, such as a liner on a cap, or a coating on internal and/or external walls of the container. In particular, liners typically refer to inserts for the caps or closures on the bottles. For example, caps with flat, disc-type polyvinyl liners, caps with flat, disc-type Teflon TPE fluorocarbon resin liners, polypropylene film foam liners, black phenolic rubber-lined closures, and a preferred liner comprising black phenolic caps with conical low-density polyethylene Poly-Seal liners that form especially good seals. The caps or closures can be constructed of the same materials as the containers, for example, amber propylene or polypropylene screw closures, polyethylene caps and/or Nalgene International TEFZEL® (ethylene-tetrafluoroethylene) closures. Coatings are typically used in reference to the outside of the container, and can include, for example, polyvinyl chloride, which is commonly used in coating acid bottles to help prevent breakage and spills. Moreover, a container, such as a clear container, can be coated with aluminum foil, Styrofoam, etc.

Moreover, the container can be constructed from a material that is transparent to light if the container is stored in another container that blocks or limits the passage of light. For example, the material of construction of the container can be clear glass or plastic, and, as discussed above, the container can be placed in a dark environment, such as a cardboard carton or a styrene package, or have a liner positioned in the container and/or a coating placed exteriorly of the container to block the transmission of light.

Materials of construction for a clear container can be glass and/or a resin, such as high density polyethylene (HDPE), low density polyethylene (LDPE), polycarbonate (PC), polyvinyl chloride (PVC), polypropylene (PP) and/or polymethylpentene (PMP). If the container is constructed from these clear materials, preferably direct UV exposure should be avoided, with the clear container being modified and/or placed in a dark environment. However, preferably, the container is constructed from a material that limits or blocks the passage of light into the container.

Still further, beneficial improvements to the metachromatic dye compositions according to the present invention can be achieved by storing the metachromatic dye composition under low temperature conditions. In particular, the metachromatic dye composition can be stored at temperature lower than about 15° C., more preferably lower than about 10° C., even more preferably lower than about 8° C. The metachromatic dye composition is preferably stored at temperatures high enough so as not to freeze the metachromatic dye composition. Preferred temperature ranges are about 15° C. to 3° C., more preferably about 10C to 4° C., more preferably about 8° C. to 4° C., and most preferably about 6° C. to 4° C.

It is noted that the herein described techniques for stabilization of the metachromatic dye compositions can be utilized in combination with each other, and such combinations of techniques can provide enhancement of the stabilization. Thus, for example, a non-aqueous metachromatic dye composition can be stored in a container that limits or blocks light penetration into the bottle, with or without any combination of techniques for removal of oxygen from the non-aqueous metachromatic dye composition, such as any combination of purging and/or use of oxygen scavengers, with or without lower storage temperatures. Moreover, the aqueous metachromatic dye composition can be adjusted to an alkaline pH with or without storage under dark conditions, and with or without storage at lower temperatures.

The concentration of the metachromatic dye in the solvent is preferably a concentration of the metachromatic dye that is in excess of that which is expected to react with the analyte to be determined, such as a polyionic polymer. For example, for the polyionic polymer, HPS-I, obtained from BetzDearborn, Inc., Trevose, Pa., at a concentration of about 0.5 ppm of polymer in the sample, the metachromatic dye composition preferably has a metachromatic dye molar concentration of at least about $9 \times 10^{-5}$ M.

It is noted that one mole of metachromatic dye reacts with 0.05 moles $SO_4^-$ (mole ratio of 1:0.05), or 0.15 moles of $COO^-$ (mole ratio of 1:0.15), or one mole of metachromatic dye to $10^{-3}$ moles HPS-1 (mole ratio of 1:0.001). Thus, the mole ratio of metachromatic dye molecules to $SO_4^-$ ranges from about 0.05 to 100, and the mole ratio of metachromatic dye molecules to $COO^-$ ranges from about 0.15 to 100. It is therefore preferred that the mole ratio of metachromatic dye to polycarboxylate and/or sulfonate groups is about 0.1 to 100, more preferably about 1 to 50, and even more preferably about 1 to 30.

The concentration of the metachromatic dye in the metachromatic dye composition is optimized so the maximum metachromatic absorbance is obtained for a polyionic material to be assayed by the following technique. Different concentrations of metachromatic dye composition are reacted with known concentrations of the polyionic material to be assayed, such as HPS-I, and a plot of absorbance vs. concentration as polyionic material is plotted. The slope of the curve is determined, and the optimum metachromatic dye composition includes a concentration of metachromatic dye, or a concentration range of metachromatic dye that provides the largest slope with a small or smallest intercept. In this manner, the metachromatic dye composition is optimized so that a small change in the concentration of the polyionic material to be assayed corresponds to a large change in absorbance over the operable absorbance range of the metachromatic dye.

A particularly preferred metachromatic dye composition is formulated by mixing 0.0844 g of metachromatic dye, e.g., pinacyanol chloride, with 250 mL of non-aqueous solvent, e.g., methanol, and adding the resulting mixture to 750 mL of viscosity increasing agent, e.g., ethylene glycol, and mixing for a sufficient amount of time to homogenize the solution, such as 30 minutes. This preferably provides a preferred composition of 25 vol % methanol and 75 vol % ethylene glycol with 0.0844 grams of pinacyanol chloride With respect to the formulation of the metachromatic dye compositions, in the case of a non-aqueous solvent system, the dye can be mixed with one or more solvents and/or one or more viscosity increasing agents. When mixed with plural solvent/viscosity materials, the metachromatic dye can be individually mixed with one or more of the materials, and subsequently mixed with any other materials in any order, or can be mixed with the total combination of materials. However, it is preferred to mix the metachromatic dye with one of the more soluble materials, most preferably the most soluble material, and then mix the resulting composition with the other solvent materials.

When mixed with solvents that do not as easily solubilize the metachromatic dye, it is preferred that the resulting composition be mixed for a sufficient period of time so that the solution is clear in that floating matter is not visible. For example, the mixing could be performed for, but not limited to, about 30 minutes, to homogenize the metachromatic dye in the solvent system.

Preferably, a dye such as pinacyanol chloride is dissolved in an oxygen-free solvent and is packaged in glass (amber) ampoules. The packaging may be sealed under vacuum for maximum stability. Storage under these conditions provides a dye with suitable stability by preventing oxygen and/or light from contacting the dye solution.

The metachromatic dye compositions of the present invention can be utilized in the determination of polyionic substances, particularly, polyionic polymers, in various environments, including, but not limited to, in aqueous environments, such as potable water, industrial systems, cooling waters, boiler systems, industrial processes, and water and waste water applications. For example, the metachromatic dye compositions can be utilized to determine polycarbonates and sulfonates disclosed in U.S. Pat. No. 4,894,346 to Myers, which is incorporated by reference hereto in its entirety. Moreover, the metachromatic dye compositions of the present invention can be utilized to monitor polymer concentrations in cooling water field samples, such as to monitor HPS-I (acrylic acid/1-allyloxy, 2-hydroxypropylsulfonate), such as disclosed in U.S. Pat. No. 4,659,481 to Chen, which is incorporated by reference hereto in its entirety, as well as PESA (polyepoxysuccinic acid disodium salt), such as disclosed in U.S. Pat. No. 5,062,962 to Brown et al., which is incorporated by reference hereto in its entirety.

To be utilizable as a metachromatic dye for analytical purposes, the metachromatic dye should be able to pass a two part test. In the first test, which is a quality of the metachromatic dye test, the metachromatic dye is mixed one part by volume with 50 parts of distilled water. The resulting dye solution should provide a visible absorbance within 1.000±0.100 AU (Absorbance Units) utilizing a 1 inch (2.54 cm) path length when measured in a spectrophotometer at 600 nm, three minutes after production of the metachromatic dye solution.

Figure 1:
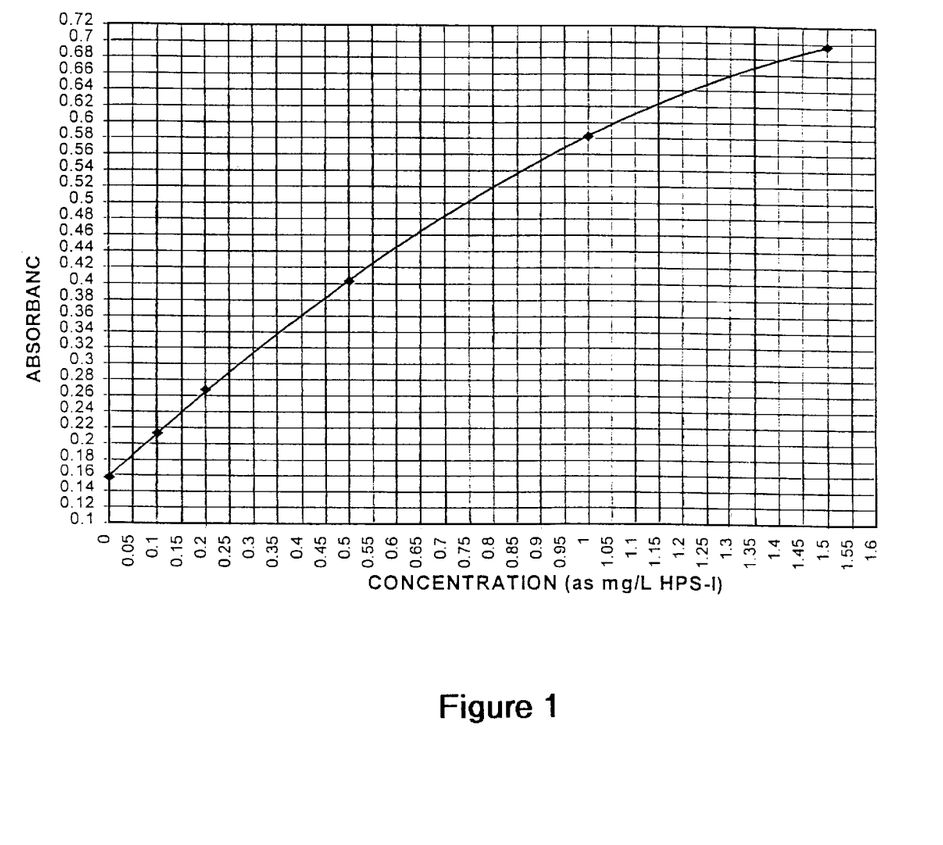
FIG. 1 depicts a calibration curve for HPS-I at 480 nm plotting absorbance vs. HPS-I concentration.

If a metachromatic dye passes the first test, it is subjected to the second test. In the second test, a 1 ppm solution of polymer in distilled water is prepared by mixing 100 ml of 1 ppm standard solution of polymer in distilled water 2 ml of buffer, preferably meta buffer (10.1 wt % EDTA (ethylendiaminetetraacetic acid) tetrasodium salt, 11 wt % potassium phosphate monobasic, and 78.9 wt % distilled water) and 5 ml of metachromatic dye. The absorbance of this solution is measured and compared to a standard calibration curve utilizing a standard 1 ppm solution of polymer in distilled water, such as illustrated in FIG. 1 and tabulated in Table 3. The measured absorbance is read against the calibration curve to determine the concentration of polymer. The concentration of polymer should be between 90% and 110% of the 1 ppm concentration. For example, in the illustrated embodiment of FIG. 1 and Table 3, the concentration should be between 0.9 and 1.1 for the measured absorbance for the metachromatic dye to pass the second test.

The determination of polyionic substances can be performed utilizing various techniques, and the following non-limiting techniques are described to provide examples of both off-line and on-line methods of performing the determination. For example, the off-line determination of HPS-I can be accomplished by diluting the sample to obtain a 0.1 to 1.5 ppm concentration of HPS-I, of which 100 ml is mixed with 2 ml of a buffer, such as meta buffer, and 5 ml of metachromatic dye composition. The mixture is preferably swirled for about 10 seconds, and at 45 to 50 seconds, 25 ml is preferably transferred to the sample cell. At as close to possible to the desired test time, such as 60 seconds, the absorbance measurement is performed, such as preferably at 480 nm in the case of HPS-I.

It is noted that glassware and sample cell are preferably rinsed with methanol after each use to avoid dye staining, then thoroughly rinsed with distilled water. Moreover, the use of disposable pipettes is preferred, as it is hard to clean and reuse pipettes.

The on-line determination of polyionic substances, such as HPS-I, can be achieved utilizing a ChemScan Analyzer, Model UV-6101, manufactured by Applied Spectrometry Associates, Inc. (ASA), Waukesha, Wis. 53186. This model allows the user to program a "read" sequence that can include up to twenty different mechanical, optical and mathematical functions. The sample volume is preferably about 10 ml, and the pathlength is preferably 0.5 inch (1.27 cm). In the test, the flow cell is flushed and filled with a sample and the cell is air purged for 5 seconds to create a small headroom for reagent additions. A buffer such as 0.5 ml of meta buffer is injected and mixed for 5 seconds before injecting 1 ml of the dye. The dye is mixed for 5 seconds and a visible absorbance scan between 400 and 650 nm is made after 20 seconds of reaction time. A multi-wavelength chemometric calibration is applied to the spectrum to determine the polymer concentration in the sample.

The invention will now be described with respect to certain examples which are merely representative of the invention and should not be construed as limiting thereof.

EXAMPLES

The invention is illustrated in the following non-limiting examples, which are provided for the purpose of representation, and are not to be construed as limiting the scope of the invention. All parts and percentages in the examples are by weight unless indicated otherwise.

Examples 1–8

The stability of pinacyanol chloride, obtained from Aldrich Chemical Co., Milwaukee, Wis., in different solvent systems is tested, with all conditions being at room temperature, using a 1 inch (2.54 cm) pathlength cuvette, by dissolving the pinacyanol chloride in each solvent system, and recording the absorbance at 600 nm in a DR2000/2010 Spectrophotometer supplied by HACH Company, Loveland, Colo., after three minutes mixing time. It is noted that where less than 100 vol % indicated for a solvent system, the balance was distilled water. Moreover, solubility issues led to the use of different concentrations of the dye in the different solutions. The concentrations and results are illustrated in Table 1, with storage of the dye solutions in amber bottles being in air for the time indicated in Table 1. Each absorbance was measured for a minimum of 6 samples, and the average value is illustrated in Table 1. The % change from day 1 shown in the Table 1, and the other tables which follow is the change of the final measured value as compared to the initial measurement.

The results illustrated in Table 1 demonstrate that Examples 2 (100 vol % ethanol), 3 (50 vol % ethylene glycol in distilled water), 5 (100 vol % methanol) and 8 (100 vol % Methyl Cellosolve) produced the most stable dye solution.

TABLE 1

Stability of Pinacyanol Chloride in Solvent Systems as a function of time in days

| Ex. No. | 1 | 2 | 3 | 4 | 5 | 6 | 7 | 8 |
|---|---|---|---|---|---|---|---|---|
| Solvent | Distilled Water | Ethanol (100%) | Ethylene Glycol (50%) | Methanol (5%) | Methanol (100%) | Methyl Cellosolve (2%) | Methyl Cellosolve (5%) | Methyl Cellosolve (100%) |
| Dye Conc. | $8.84 \times 10^{-5}M$ | $1.1 \times 10^{-3}M$ | $9.2 \times 10^{-5}M$ | $8.93 \times 10^{-5}M$ | $1.79 \times 10^{-3}M$ | $9.0 \times 10^{-5}M$ | $9.0 \times 10^{-5}M$ | $1.8 \times 10^{-3}M$ |

| Time (days) | \multicolumn{8}{c}{Absorbance at 600 nm} |
|---|---|---|---|---|---|---|---|---|
| 1 | 1.370 | 1.058 | 1.437 | 1.446 | 1.446 | 1.445 | 1.445 | 1.445 |
| 2 | 1.318 | | | | | | | |
| 3 | 1.289 | | | | | | | |
| 4 | 1.250 | | | | | | | |
| 5 | 1.242 | | | | | | | |
| 6 | | | | 1.229 | 1.418 | 1.364 | 1.365 | 1.419 |
| 20 | | | | | | | | 1.421 |
| 35 | | | 1.428 | | | | | |
| 58 | | | | | 1.464 | | | |
| 82 | | 1.057 | | | | | | |

TABLE 1-continued

Stability of Pinacyanol Chloride in Solvent Systems as a function of time in days

| %Change from day 1 | −9.3 | −0.1 | −0.6 | −15.0 | 1.2 | −5.6 | −5.5 | −1.7 |
|---|---|---|---|---|---|---|---|---|

Examples 9–11

0.0844 g pinacyanol chloride is dissolved in a solvent system of 250 milliliters (ml) of technical grade methanol obtained from Coyne Chemical, Croydon, Pa., and 750 ml of ethylene glycol, obtained from Fischer Scientific, Pittsburgh, Pa. (Laboratory Grade indicated to be typically>99% pure), for a total volume of 1 liter. The solutions were stored at three temperatures of 4° C., 20° C. and 40° C. for the time periods indicated in Table 2. Storage of the samples and the absorbance measurements were made in a similar manner as set forth in Example 1 except all experiments were run a minimum of three times with the average shown in Table 2. These examples show that metachromatic dye compositions according to the present invention are stable for lengthy periods, including about 7.5 months.

TABLE 2

Stability of Pinacyanol Chloride
in 25 vol %/75 vol % Methanol/Ethylene Glycol (1:3)
Stored at Different Temperatures

| Ex. No. | 9 | 10 | 11 |
|---|---|---|---|
| Temperature | 40° C. | 20° C. | 4° C. |
| Time (days) | Absorbance at 600 nm | | |
| 1 | 1.011 | 1.011 | 1.011 |
| 48 | 1.025 | 1.040 | 1.014 |
| 55 | 1.021 | 1.028 | 1.051 |
| 83 | 1.079 | 1.090 | 1.087 |
| 123 | 0.948 | 0.889 | 0.973 |
| 166 | 1.027 | 0.995 | 1.083 |
| 194 | 0.989 | 0.989 | 1.094 |
| 230 | 0.977 | 0.942 | 1.077 |
| % Change from day 1 | −3.4 | −6.8 | 6.5 |

Example 12

A calibration curve for HPS-I, obtained from BetzDearborn Division of Hercules Incorporated, Trevose, Pa., was prepared by reacting different concentrations of the HPS-I dissolved in distilled water mixed with 2 ml of META buffer and 5 ml of the pinacyanol chloride solution in methanol/ ethylene glycol of Examples 9–11 except that the methanol is Certified A.C.S. Grade Methanol with a purity of 99.8% obtained from Fischer Scientific, Pittsburgh, Pa. The visible absorbance at 480 nm was measured after reacting for 1 minute using a DR2000/2010 Spectrophotometer available from HACH Company, Loveland, Colo. A 1-inch (2.54 pathlength cuvette holding a total volume of 25 ml was utilized, and the dye solutions were stored in amber bottles in air for the duration of all experiments. Each absorbance was measured for a minimum of 3 samples, and the average value is illustrated in Table 3, and the resulting calibration curve is shown in FIG. 1.

TABLE 3

| Concentration (ppm) of HPS-I | Absorbance @ 480 nm |
|---|---|
| 0 | 0.157 |
| 0.1 | 0.213 |
| 0.2 | 0.267 |
| 0.5 | 0.403 |
| 1.0 | 0.582 |
| 1.5 | 0.696 |

Examples 13–27

The pinacyanol chloride solution in a 25:75 vol % of methanol to ethylene glycol of Examples 9–11 was stored for varying period of times. The stored pinacyanol chloride solutions were prepared as in Example 12, and then reacted with the same known concentration of HPS-I, and the visible absorbance was measured in the same manner as in Example 12.

The solution having a known concentration of HPS-I was prepared by mixing HPS-I in distilled water to give a concentration of 1 ppm HPS-I to achieve a test solution that provides an absorbance reading within the calibration range of 0–1.5 ppm, as illustrated in FIG. 1. The results are shown in Table 4.

TABLE 4

Concentration of HPS-I Recovered as a Function of Time (in days) Using Pinacyanol Chloride in 25 Vol% MeOH:75 Vol% Ethylene Glycol.

| Example No. | Time (Days) | Temperature (° C.) | Absorbance (@480 nm) | Concentration Recovered, ppm |
|---|---|---|---|---|
| 13 | 83 | 40 | 0.605 | 1.07 |
| 14 | 83 | 20 | .0594 | 1.03 |
| 15 | 83 | 4 | 0.607 | 1.07 |
| 16 | 123 | 40 | 0.591 | 1.02 |
| 17 | 123 | 20 | 0.584 | 1.00 |
| 18 | 123 | 4 | 0.588 | 1.01 |
| 19 | 166 | 40 | 0.593 | 1.03 |
| 20 | 166 | 20 | 0.579 | 0.99 |
| 21 | 166 | 4 | 0.603 | 1.07 |
| 22 | 194 | 40 | 0.594 | 1.03 |
| 23 | 194 | 20 | 0.575 | 0.97 |
| 24 | 194 | 4 | 0.604 | 1.07 |
| 25 | 230 | 40 | 0.590 | 1.01 |
| 26 | 230 | 20 | 0.572 | 0.96 |
| 27 | 230 | 4 | 0.595 | 1.03 |

Examples 28–56

The stability of $9 \times 10^{-5}$ pinacyanol chloride, obtained from Aldrich Chemical Co., Milwaukee, Wis., is tested in aqueous media as shown in Tables 5–14, with all conditions being at room temperature, using a 1 inch (2.54 cm) pathlength cuvette, by dissolving the pinacyanol chloride in an aqueous system, and recording the absorbance at 600 nm in the above-noted DR2000/20 10 Spectrophotometer after a 3 minute mixing time. Storage of the dye solutions is in amber bottles in air for the time indicated in the tables. Each absorbance was measured in at least duplicate, and the average value is illustrated in the tables.

Table 5 shows the stability of pinacyanol chloride in the presence of strong base.

Table 6 shows the stability of pinacyanol chloride in the presence of oxygen scavenger.

Table 7 shows the stability of pinacyanol chloride in the presence of oxygen scavenger.

Table 8 shows the stability of pinacyanol chloride in the presence of strong based and oxygen scavenger.

Table 9 shows the stability of pinacyanol chloride in the presence of oxygen scavenger.

Table 10 shows the stability of pinacyanol chloride in the presence of oxygen scavenger.

Table 11 shows the stability of pinacyanol chloride in the presence of strong base and oxygen scavenger.

Table 12 shows the stability of pinacyanol chloride in the presence of buffer.

Table 13 shows the stability of pinacyanol chloride in the presence of strong acid.

Table 14 shows the stability of pinacyanol chloride in the presence of oxygen scavenger.

As can be seen from the results depicted in these Tables 5–14, the presence of a strong acid or oxygen scavenger per se, the dye discolors quickly. In the presence of 0.15 wt/wt of NaOH, the dye fading is minimal (~3% in 6 days).

TABLE 5

Stability of Pinacyanol Chloride in the Presence of Strong Base

| Ex. No. | Time (days) | System | Absorbance @600 nm | % change from Day 1 | Observations |
|---|---|---|---|---|---|
| 28 | 1 | Distilled Water (DI) + 1 ml NaOH(1N) | 1.196 |  | Dark Purple, No Change |
| 29 | 2 | DI + 1 ml NaOH(1N) | 1.213 | 1.4 | Dark Purple, No Change |
| 30 | 6 | DI + 1 ml NaOH (1N) | 1.164 | −2.7 | Dark Purple, No Change |

TABLE 6

Stability of Pinacyanol Chloride in the Presence of Oxygen Scavenger

| Ex. No. | Time (days) | System | Absorbance @600 nm | % change from Day 1 | Observations |
|---|---|---|---|---|---|
| 31 | 1 | DI + 0.1 gm $Na_2SO_3$ | 1.089 |  | Sky Blue, Significant Color Change |
| 32 | 2 | DI + 0.1 gm $Na_2SO_3$ | 1.14 | 4.7 | Sky Blue, Significant Color Change |
| 33 | 6 | DI + 0.1 gm $Na_2SO_3$ | 0.741 | −32 | Sky Blue, Significant Color Change |

TABLE 7

Stability of Pinacyanol Chloride in the Presence of Oxygen Scavenger

| Ex. No. | Time (days) | System | Absorbance @600 nm | % change from Day 1 | Observations |
|---|---|---|---|---|---|
| 34 | 1 | DI + 0.2 gm $Na_2SO_3$ | 1.03 |  | Sky Blue, Significant Color Change |
| 35 | 2 | DI 0.2 gm $Na_2SO_3$ | 0.12 | −88.3 | Sky Blue, Significant Color Change |
| 36 | 6 | DI + 0.2 gm $Na_2SO_3$ | 0.557 | −44 | Precipitation |

TABLE 8

Stability of Pinacyanol Chloride in the Presence of Strong Base and Oxygen Scavenger

| Ex. No. | Time (days) | System | Absorbance @600 nm | % change from Day 1 | Observations |
|---|---|---|---|---|---|
| 37 | 1 | DI + 0.1 gm $Na_2SO_3$ + 1 mL NaOH(1N) | 1.07 | Significant | Sky Blue, Color Change |
| 38 | 2 | DI + 0.1 gm $Na_2SO_3$ + 1 mL NaOH(1N) | 1.534 | 43.4 Significant | Sky Blue, Color Change |
| 39 | 6 | DI + 0.1 gm $Na_2SO_3$ + 1 mL NaOH(1N) | 0.858 | −19.8 Significant | Sky Blue, Color Change |

TABLE 9

Stability of Pinacyanol Chloride in the Presence of Oxygen Scavenger

| Ex. No. | Time (days) | System | Absorbance @600 nm | % change from Day 1 | Observations |
|---|---|---|---|---|---|
| 40 | 1 | DI + 0.1 gm $NaNO_2$ | 0.884 | | Sky Blue, Significant Color Change |
| 41 | 2 | DI + 0.1 gm $NaNO_2$ | 0.719 | −18.7 | Sky Blue, Significant Color Change |
| 42 | 6 | DI + 0.1 gm $NaNO_2$ | 0.713 | −19.3 | Precipitation |

TABLE 10

Stability of Pinacyanol Chloride in the Presence of Oxygen Scavenger

| Ex. No. | Time (days) | System | Absorbance @600 nm | % change from Day 1 | Observations |
|---|---|---|---|---|---|
| 43 | 1 | DI + 0.2 gm $NaNO_2$ | 1.16 | | Sky Blue, Significant Color Change |
| 44 | 2 | DI + 0.2 gm $NaNO_2$ | 1.117 | −3.7 | Sky Blue, Significant Color Change |
| 45 | 6 | DI + 0.2 gm $NaNO_2$ | 0.871 | −25 | Precipitation |

TABLE 11

Stability of Pinacyanol Chloride in the Presence of Strong Base and Oxygen Scavenger

| Ex. No. | Time (days) | System | Absorbance @600 nm | % change from Day 1 | Observations |
|---|---|---|---|---|---|
| 46 | 1 | DI + 0.1 gm $NaNO_2$ + 1 mL NaOH(1N) | 0.893 Significant | | Sky Blue, Color Change |
| 47 | 2 | DI + 0.1 gm $NaNO_2$ + 1 mL NaOH (1N) | 0.908 Significant | 1.7 | Sky Blue, Color Change |
| 48 | 6 | DI + 0.1 gm $NaNO_2$ + 1 mL NaOH (1N) | 1.020 Significant | 14 | Sky Blue, Color Change |

TABLE 12

Stability of Pinacyanol Chloride in the Presence of Strong Base and

| Ex. No. | Time (days) | System | Absorbance @600 nm | % change from Day 1 | Observations |
|---|---|---|---|---|---|
| 49 | 1 | Meta Buffer | 1.038 | | Dark Purple, No Change |
| 50 | 2 | Meta Buffer | 1.701 | 63.9 | Precipitation |
| 51 | 6 | Meta Buffer | 0.923 | −11 | Precipitation |

[1]Meta buffer includes 10.1% EDTA (Ethylendiaminetetraacetic acid) Tetrasodium Salt, 11% Potassium Phosphate Monobasic, and 78.9% Distilled Water.

TABLE 13

Stability of Pinacyanol Chloride in the Presence of Strong Acid

| Ex. No. | Time (days) | System | Absorbance @ 600 nm | % change from Day 1 | Observations |
|---|---|---|---|---|---|
| 52 | 1 | DI + 2 drops $H_2SO_4$ (10N) | | | Colorless |
| 53 | 2 | DI + 2 drops $H_2SO_4$ (10N) | | | Colorless |
| 54 | 6 | DI + 2 drops $H_2SO_4$ (10N) | | | Colorless |

TABLE 14

Stability of Pinacyanol Chloride in the Presence of Oxygen Scavenger

| Ex. No. | Time (days) | System | Absorbance @ 600 nm | % change from Day 1 | Observations |
|---|---|---|---|---|---|
| 55 | 1 | DI + 0.1 gm hydroquinone | 1.287 | | |
| 56 | 6 | DI + 0.1 gm hydroquinone | | | Light Brown, Significant Color Change |

Examples 57–61

The stability of pinacyanol chloride, obtained from Aldrich Chemical Co., Milwaukee, Wis., in different solvent systems is tested, with all conditions being at room temperature, using a 1 inch (2.54 cm) pathlength cuvette, by dissolving the pinacyanol chloride in each solvent system, and recording the absorbance at 600 nm in a DR2000/2010 Spectrophotometer supplied by HACH Company, Loveland, Colo., after three minutes mixing time. It is noted that where less than 100 vol % indicated for a solvent system, the balance was distilled water. Moreover, solubility issues led to the use of different concentrations of the dye in the different solutions. Storage of the dye solutions is in amber bottles in air at 4° C. for the time indicated in the tables. Each absorbance was measured for a minimum of 6 samples, and the average value is illustrated in the Table 15.

TABLE 15

Stability of Pinacyanol Chloride in Solvent Systems as a function of time in days at 4° C.

| Ex. No. | 57 | 58 | 59 | 60 | 61 |
|---|---|---|---|---|---|
| Solvent | Methanol | Methanol | Methyl | Methyl | Methyl |

TABLE 15-continued

Stability of Pinacyanol Chloride in Solvent Systems as a function of time in days at 4° C.

| | (5 vol %) | (100 vol %) | Cellosolve (2 vol %) | Cellosolve (5 vol %) | Cellosolve (100 vol %) |
|---|---|---|---|---|---|
| Dye Conc. | $8.93 \times 10^{-5}M$ | $1.79 \times 10^{-3}M$ | $9.0 \times 10^{-5}M$ | $9.0 \times 10^{-5}M$ | $1.8 \times 10^{-3}M$ |
| Time (days) | | | Absorbance at 600 nm | | |
| 1 | 1.489 | 1.469 | 1.439 | 1.445 | 1.445 |
| 6 | 1.426 | 1.462 | 1.364 | 1.365 | 1.419 |
| 20 | | | | | 1.421 |
| 22 | | 1.446 | | | |
| % Change from day 1 | −4.2 | −1.6 | −5.2 | −5.5 | −1.7 |

Although data shows promising results, it is noted that storage of the metachromatic dye compositions under refrigeration in the field is not as desirable as storage under ambient conditions.

Examples 62–63

The stability of pinacyanol chloride, obtained from Aldrich Chemical Co., Milwaukee, Wis., in distilled water, with purging with $N_2$ gas in room temperature (20° C.) and low temperature, i.e., 4° C., studies utilizing conditions as set forth in Examples 57–61. The results are shown in Table 16

TABLE 16

Stability of Pinacyanol Chloride in Distilled Water Using Nitrogen Purge At Room Temperature and 4° C.

| | Ex. No. | |
|---|---|---|
| Ex. No. | 62 (20°) | 63 (4° C.) |
| Time (days) | Absorbance at 600 nm | |
| 1 | 1.463 | 1.463 |
| 7 | 1.392 | 1.466 |
| 23 | | 1.446 |
| % Change from day 1 | −4.8 | −1.2 |

Although data shows promising results, it is noted that storage of the metachromatic dye compositions under refrigeration in the field is not as desirable as storage under ambient conditions. Moreover, stabilization by purging the metachromatic dye composition after each use is not as desirable as stabilization with a technique that does not require repeated efforts on the part of field personnel.

Example 64

Varying concentrations of pinacyanol chloride, obtained from Aldrich Chemical Co., Milwaukee, Wis., in a solution of 25 vol % methanol, Certified A.C.S. Grade Methanol with a purity of 99.8% obtained from Fischer Scientific, Pittsburgh, Pa., to 75 vol % ethylene glycol, obtained from Fischer Scientific, Pittsburgh, Pa. (Laboratory Grade indicated to be typically>99%, are prepared, and reacted with 0.2 mg/L and 1.0 mg/L HPS-I, obtained from BetzDearborn Division of Hercules Incorporated, Trevose, Pa., with the visible absorbance being measured in the same manner as in Example 12. The results are illustrated in Table 17.

TABLE 17

| Conc (M) Pinacyanol Chloride in 25% Methanol:75% Ethylene Glycol | Absorbance @ 480 nm 0.2 mg/L HPS-I | Absorbance @ 480 nm 1.0 mg/L HPS-I | Linear Equation |
|---|---|---|---|
| $1.07 \times 10^{-4}$ | 0.175 | 0.451 | y = 0.345x + 0.106 |
| $1.43 \times 10^{-4}$ | 0.236 | 0.487 | y = 0.3138x + 0.1733 |
| $2.14 \times 10^{-4}$ | 0.309 | 0.604 | y = 0.3688x + 0.2353 |
| $2.17 \times 10^{-4}$ | 0.318 | 0.621 | y = 0.3788x + 0.2423 |
| $2.91 \times 10^{-4}$ | 0.431 | 0.719 | y = 0.36x + 0.359 |
| $3.58 \times 10^{-4}$ | 0.447 | 0.810 | y = 0.4538x + 0.3563 |

Figure 2:
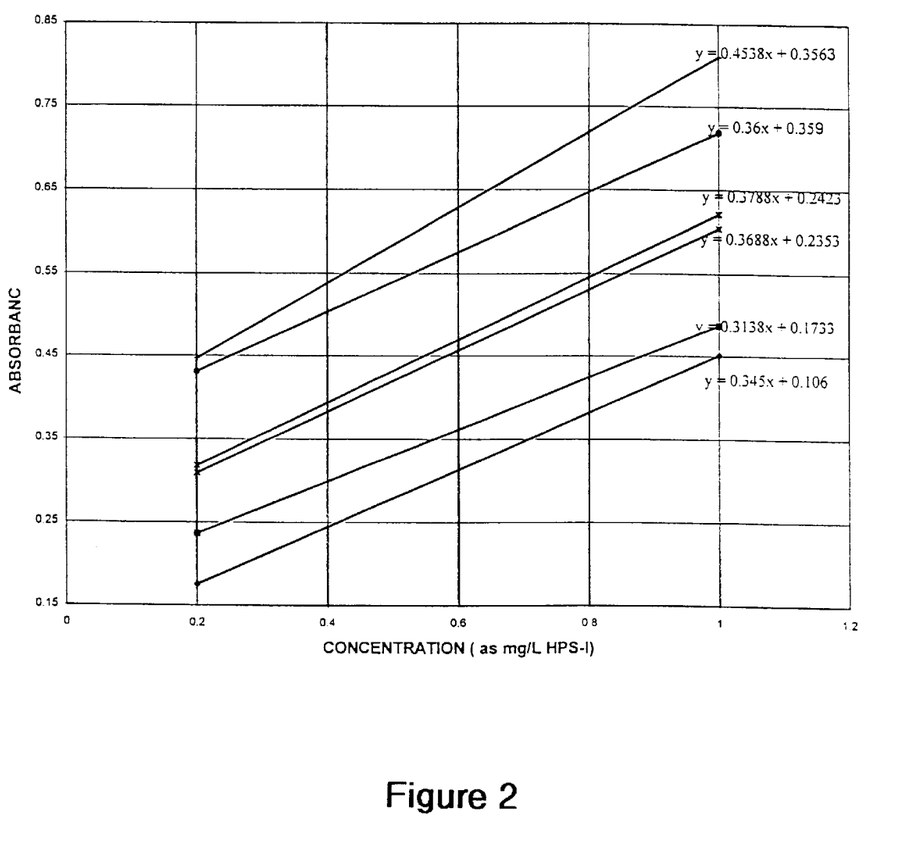
FIG. 2 depicts plots of absorbance vs. concentration for HPS-I plotting absorbance vs. HPS-I concentration.

A plot of absorbance vs. concentration is plotted, as illustrated in FIG. 2. It is noted that as the concentration of the dye solution increases, the curves in FIG. 2 decrease. The slope of the curve is determined, and the optimum metachromatic dye concentration provides a small change in the concentration of the HPS-I providing a large change in absorbance. This concentration provides a compromise between the steepest slope and the smallest intercept, so that a small change in the concentration of HPS-I in a water sample will correspond to a large change in absorbance. Thus, a molar concentration of $2.17 \times 10^{-4}$ is seen to be a preferred concentration of the pinacyanol chloride. In particular, a dye concentration of $2.17 \times 10^{-4}$ M not only gives the highest sensitivity (as seen by the increase in the slope on the calibration curve in FIG. 2) but also produces the best accuracy in the calibration range (0.3 to 0.6 absorbance units for the recommended spectral range for a HACH DR2000/20 10).

Example 65

The stability of metachromatic dye compositions in sealed glass ampoules was tested utilizing water purged with argon as follows.

The water used is distilled water which is purged thoroughly with argon to remove dissolved oxygen.

Three metachromatic dye compositions are prepared including a metachromatic dye concentration of 35 mg/L ($9.0 \times 10^{-5}$ M) in the following three solvent systems:
  a. 100% aqueous solution
  b. 50% v/v water/propylene glycol
  c. 50% v/v water/ethylene glycol.

The solutions were packaged in AccuVac ampoules, obtained from Hach Company, Loveland, Colo., and Voluette ampoules, obtained from Hach Company, Loveland, Colo., immediately after preparation. AccuVac ampoules were filled with 1 mL of the dye solution, and the total volume of the ampoule is 13.5 mL. The Voluette ampoules are filled with 2 mL of the dye solution, and the total volume of the ampoule is 2.2 mL.

The Voluette ampoules are amber in color. The AccuVac ampoules are placed into styrofoam containers as soon as they were prepared to protect them from light.

The packaging of the Voluette is under atmospheric pressure, whereas the AccuVac is under vacuum.

Results of the tests are shown in Table 18 for the metachromatic dye compositions, and in Table 19 for reaction with a HPS-I standard solution.

With regard to testing the AccuVac ampoules, it is noted that a single AccuVac ampoule gives vastly different absorbances depending on the orientation in the cell holder. Absorbances varied from 0.307 to 0.358 AU or 0.05 AU for the test which is ~15% error. The reasons for these significant variances include that the ampoules did not have a consistent diameter, the ampoules were becoming stained with the dye, i.e., the dye precipitated, and imperfections in the quality of the glass.

The dye in the Voluette ampoules continued to show stability after 2.5 months time.

TABLE 18

| Quality Check (@ 600 nm) of dye solutions (25 mL of DI water + 2 mL of dye solution) | | | | | |
|---|---|---|---|---|---|
| Solvent | $H_2O$ AccuVac | $H_2O$/ Ethylene Glycol AccuVac | $H_2O$/ Propylene Glycol AccuVac | $H_2O$/ Ethylene Glycol Voluette | $H_2O$/ Propylene Glycol Voluette |
| Time (Days) | Absorbance @ 600 nm | | | | |
| 1 | 1.587 | 1.722 | 1.782 | 1.736 | 1.707 |
| 4 | 1.301 | 1.479 | 1.519 | 1.731 | 1.691 |
| 6 | 1.147 | 1.400 | 1.414 | 1.633 | 1.664 |
| 20 | | | | 1.622 | 1.674 |
| 82 | | | | 1.625 | 1.663 |
| % Change from day 1 | −28 | −19 | −21 | −6.4 | 2.6 |

TABLE 19

| Quality Check (@ 480 nm) of 25 mL of a 0.5 ppm HPS-I standard solution + 1 mL Meta Buffer + 2 mL of dye solution | | | | |
|---|---|---|---|---|
| Time | $H_2O$/Ethylene Glycol AccuVac | $H_2O$/Propylene Glycol AccuVac | $H_2O$/Ethylene Glycol Voluette | $H_2O$/Propylene Glycol Voluette |
| 6 | 0.345 | 0.328 | 0.343 | 0.334 |
| 82 | | | 0.332 | 0.328 |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A stabilized aqueous solution of metachromatic dye comprising metachromatic dye in an aqueous solvent, said metachromatic dye comprising pinacyanol chloride, said aqueous solution having a metachromatic dye stabilizing pH, and a percent change in absorbance of less than about 10% when stored for a period of about one week.

2. The aqueous solution of metachromatic dye according to claim 1 wherein said aqueous solvent has a pH of at least about 8.

3. The aqueous solution of metachromatic dye according to claim wherein said aqueous solvent has a pH of at least about 10.

4. The aqueous solution of metachromatic dye according to claims wherein said aqueous solvent has a pH of at least about 11.

5. The aqueous solution of metachromatic dye according to claim 1 wherein said aqueous solvent has a pH of about 8 to 14.

6. The aqueous solution of metachromatic dye according to claim 5 wherein said aqueous solvent has a pH of about 11 to 12.

7. The aqueous solution of metachromatic dye according to claim 6 wherein said aqueous solvent has a pH of about 11 to 11.5.

8. The aqueous solution of metachromatic dye according to claim 1 including at least one basic material.

9. The aqueous solution of metachromatic dye according to claim 8 wherein said at least one basic material comprises a buffer.

10. The aqueous solution of metachromatic dye according to claim 8 wherein said at least one basic material comprises at least one of sodium hydroxide, potassium hydroxide and lithium hydroxide.

11. The aqueous solution of metachromatic dye according to claim 10 wherein said at least one basic material comprises sodium hydroxide.

12. The aqueous solution of metachromatic dye according to claim 1 further including at least one non-aqueous solvent.

13. The aqueous solution of metachromatic dye according to claim 1 further including at least one oxygen scavenger.

14. The aqueous solution of metachromatic dye according to claim 1 wherein the aqueous solution is substantially free of oxygen.

15. A metachromatic dye solution for analytical determination of at least one polyionic substance comprising metachromatic dye and non-aqueous solvent, the metachromatic dye comprising pinacyanol chloride, the solution being substantially free of water, said metachromatic dye solution including a concentration of said metachromatic dye which provides maximum metachromatic absorbance for the at least one polyionic substance when said at least one polyionic substance is present at a concentration of 0.1 to 1.5 ppm, and said non-aqueous solvent comprises at least one of methanol, ethanol, butanol, isopropanol, propanol, ethylene glycol, methylcellosolve, hexane, pentane, heptane, toluene, xylene, benzene, dichlorobenzene, acetone, ethyl acetate, diethyl ether, acetonitrile and dimethylsulfoxide.

16. The metachromatic dye solution according to claim 15 wherein said non-aqueous solvent comprises at least one of methylcellosolve, hexane, pentane, heptane, toluene, xylene, benzene, dichlorobenzene, acetone, ethyl acetate, diethyl ether, acetonitrile, dimethylsulfoxide.

17. The metachromatic dye solution according to claim 15 wherein said non-aqueous solvent comprises at least one of methanol, ethanol, butanol, isopropanol, propanol and ethylene glycol.

18. The metachromatic dye solution according to claim 15 wherein said non-aqueous solvent has a density at 25° C. of about 0.95 to 1.2 g/cm³.

19. The metachromatic dye solution according to claim 18 wherein said non-aqueous solvent has a density at 25° C. of about 1 to 1.1 g/cm³.

20. The metachromatic dye solution according to claim 19 wherein said non-aqueous solvent has a density at 25° C. of about 1 to 1.05 g/cm³.

21. The metachromatic dye solution according to claim 15 wherein said non-aqueous solvent comprises a mixture of non-aqueous solvents.

22. The metachromatic dye solution according to claim 21 wherein said mixture of non-aqueous solvents comprises a mixture of methanol and ethylene glycol.

23. The metachromatic dye solution dye according to claim 21 wherein said mixture of non-aqueous solvents comprises a mixture containing 25 vol % methanol and 75 vol % ethylene glycol.

24. The metachromatic dye solution according to claim 18 wherein said non-aqueous solvent comprises a mixture of non-aqueous solvents.

25. The metachromatic dye solution according to claim 24 wherein said mixture of non-aqueous solvents comprises a mixture of methanol and ethyene glycol.

26. The metachromatic dye solution according to claim 15 wherein the solution is free of water.

27. The metachromatic dye solution dye according to claim 15 wherein said non-aqueous solvent comprises high purity solvent.

28. The metachromatic dye solution according to claim 15 further including an oxygen scavenger.

29. The metachromatic dye solution according to claim 15 in the substantial absence of oxygen.

30. The metachromatic dye solution according to claim 15 wherein the solution is purged with an inert gas.

31. A container including therein the aqueous solution of metachromatic dye recited in claim 1.

32. The container according to claim 31 wherein the container at least reduces the transmission of light.

33. The container according to claim 32 wherein the container prevents the transmission of light.

34. A container including therein the aqueous solution of metachromatic dye recited in claim 6.

35. The container according to claims wherein the container at least reduces the transmission of light.

36. The container according to claim 35 wherein the container prevents the transmission of light.

37. A container including therein the solution of metachromatic dye recited in claim 15.

38. The container according to claim 37, wherein the container at least reduces the transmission of light.

39. The container according to claim 38, wherein the container prevents the transmission of light.

40. A container including therein the solution of metachromatic dye recited in claim 18.

41. The container according to claim 40, wherein the container at least reduces the transmission of light.

42. The container according to claim 41 wherein the container prevents the transmission of light.

43. A container including therein the solution of metachromatic dye recited in claim 24.

44. The container according to claim 43 wherein the container at least reduces the transmission of light.

45. The container according to claim 44 wherein the container prevents the transmission of light.

46. A container including therein the solution of metachromatic dye recited in claim 26.

47. The container according to claim 46 wherein the container at least reduces the transmission of light.

48. The container according to claim 47 wherein the container prevents the transmission of light.

49. A metachromatic dye solution comprising metachromatic dye and non-aqueous solvent, the metachromatic dye comprising pinacyanol chloride, the solution being substantially free of water, said non-aqueous solvent having a density at 25° C. of about 0.95 to 1.2 $g/cm^3$ and comprising a mixture of methanol and ethylene glycol.

* * * * *